(12) United States Patent
Teng et al.

(10) Patent No.: US 6,169,055 B1
(45) Date of Patent: Jan. 2, 2001

(54) CATALYST FOR PRODUCTION OF ACROLEIN, METHOD FOR PRODUCTION THEREOF, AND METHOD FOR PRODUCTION OF ACROLEIN

(75) Inventors: Yonghong Teng, Nara-ken; Tetsuhiko Kobayashi, Ikeda; Atsushi Ueda, Nishinomiya, all of (JP)

(73) Assignee: Agency of Industrial Science & Technology, Ministry of International Trade & Industry, Tokyo (JP)

( * ) Notice: Under 35 U.S.C. 154(b), the term of this patent shall be extended for 0 days.

(21) Appl. No.: 09/203,402

(22) Filed: Dec. 2, 1998

(30) Foreign Application Priority Data

Jan. 12, 1998 (JP) .................................................. 10-018273

(51) Int. Cl.$^7$ .............................. B01J 21/06; C07C 45/33
(52) U.S. Cl. .......................... 502/243; 502/258; 502/330; 502/338; 568/475
(58) Field of Search .................................... 568/449, 459, 568/470, 475; 502/243, 258, 330, 338

(56) References Cited

PUBLICATIONS

Wataru Ueda, "Selective Oxidation of Alkanes and Metal Oxide Catalyst", Journal of Hyomen, vol. 35 No. 1, 1997, pp. 13–24 (With Partial English Translation).

Yusaku Takita, "Current Trend in Oxidation Catalyst: Paraffin Oxidation Study", Journal of Trend and Prospect of Catalyst Technology, 1995, pp. 33–42 (With Partial English Translation).

Yunghong Teng, et al. "Reaction Pathways for the Oxygenates Formation from Propane and Oxygen Over Potassium–Modified Fe/SiO$_2$ Catalysts", Catalysts Letters, vol. 55, 1998, pp. 33–38.

M.M. Bettahar, et al. "On the Partial Oxidation of Propane and Propylene on Mixed Metal Oxide Catalysts", Applied Catalysts A: General, vol. 145, 1996, pp. 1–48.

C. Batiot, et al. "The Role of Reactant and Product Bond Energies in Determining Limitations to Selective Catalytic Oxidations", Applied Catalysis A: General, vol. 137, 1996, pp. 179–191.

*Primary Examiner*—Sreeni Padmanabhan
(74) *Attorney, Agent, or Firm*—Oblon, Spivak, McClelland, Maier & Neustadt, P.C.

(57) ABSTRACT

A catalyst for producing acrolein by oxidizing ethane contains silicon, iron, an alkali metal, and oxygen. A method for producing acrolein includes the step of oxidizing ethane in the presence of the catalyst and a method for producing the catalyst includes the steps of mixing porous silicon oxide with an iron compound and an alkali metal compound and calcining the resultant mixture.

17 Claims, No Drawings

CATALYST FOR PRODUCTION OF ACROLEIN, METHOD FOR PRODUCTION THEREOF, AND METHOD FOR PRODUCTION OF ACROLEIN

BACKGROUND OF THE INVENTION

1. Field of the Invention

This invention relates to a catalyst for the production of acrolein by the oxidation of ethane, a method for the production of the catalyst, and a method for the production of acrolein by the use of the catalyst.

2. Description of the Prior Art

Acrolein, an important raw material for the chemical industry, is generally produced by oxidation of propylene. The cost of producing acrolein is therefore high. If a method for producing acrolein directly from ethane, a cheap and abundantly available substance and oxygen is developed, it will permit a significant decrease in the cost of production. A growing need is therefore felt for the development of such a method.

Known catalysts for producing acrolein from propylene or propane include one containing copper oxide as an active component, one using a molybdenum-bismuth complex oxide as an active component, one containing molybdenum, vanadium, phosphorus, etc., and one containing molybdenum, vanadium, niobium, tellurium, etc. The production of acrolein from ethane, however, cannot be attained by using any of these catalysts.

As catalysts for producing acetaldehyde directly from ethane and oxygen, there are known one containing boron, phosphorus, etc. and one containing vanadium, silicon, etc. As catalysts for producing acetic acid from ethane and oxygen, there are known one containing vanadium, titanium, molybdenum, phosphorus, etc. and one containing molybdenum, vanadium, niobium, etc. No catalyst, however, has been available for directly producing acrolein from ethane and oxygen.

A method for producing acrolein from ethane, an inexpensive substance, and oxygen on a commercial scale has not been established.

This invention has an object of providing a technique capable of stably and inexpensively producing acrolein with high efficiency directly from ethane and oxygen.

The inventors, through a study conducted with a view to accomplishing this object, first learned that (A) a composite (or complex oxide) which has iron and silicon oxide, readily available substances with very low toxicity, as components forms an excellent catalyst for producing formaldehyde from methane and that (B) the composite mentioned above is capable of functioning as a catalyst for producing acrolein from propane. After continuing the study further based on this knowledge, they discovered that a composite (or complex oxide) resulting from the addition of an alkali metal to the composite (or complex oxide) mentioned above excels in stability and functions satisfactorily as a catalyst for efficiently producing acrolein from ethane and oxygen as raw materials.

SUMMARY OF THE INVENTION

This invention relates to a catalyst containing silicon, iron, an alkali metal, and oxygen and serving the purpose of producing acrolein from ethane as a raw material and to a method for producing acrolein by oxidizing ethane in the presence of this catalyst. This invention further relates to a method for producing a catalyst containing silicon, iron, an alkali metal, and oxygen by impregnating porous silicon oxide with a mixture of an aqueous water-soluble iron compound solution and an aqueous alkali metal solution or sequentially with said two aqueous solutions, thereby inducing adhesion of iron and an alkali component to the porous silicon oxide, and calcining the resultant porous silicon carbide having iron and alkali metal deposited thereon and to a method for producing a catalyst containing ferrosilicon, an alkali metal, and oxygen by forming a mixture of silicon and iron by the sol-gel process from a mixture of at least one member selected from the group consisting of water-soluble iron compounds and organic iron compounds with tetraethyl silicate, drying the resultant mixture, calcining the dried mixture in the presence of oxygen, and impregnating the product of this calcination with an aqueous alkali metal solution, then drying the product of impregnation, and calcining the dried product of impregnation in the presence of oxygen.

DESCRIPTION OF THE PREFERRED EMBODIMENTS

The catalyst of this invention for the production of acrolein is formed of an amorphous complex oxide using silicon, iron, an alkali metal, and oxygen as component elements.

Silicon in the form of silicon oxide is the main component of the catalyst. So long as it has a porous texture, the silicon oxide can be a product of the sol gel process or the gaseous-phase reaction process, or be a commercially available silica gel.

The iron and the alkali metal are thought to act as active components of the catalyst because they are at least partly carried in a highly dispersed state as iron ion ($Fe^{3+}$) and an alkali metal ion ($M^+$) forming the oxide on the surface (inner pore surfaces) of the porous silicon oxide.

Though not particularly limited, the process of producing the catalyst of this invention for the production of acrolein is generally as follows.

First, a catalyst precursor is obtained by incorporating iron ions in porous silicon oxide. Though the production of this catalyst precursor is not limited to a particular method, it can be attained, for example, by immersing porous silicon oxide (having a specific surface area in the approximate range of 10–1000 $m^2/g$, preferably 30–600 $m^2/g$) in an aqueous solution of such a water-soluble iron compound as, for example, iron nitrate, iron sulfate, iron chloride, iron phosphate, iron acetate, iron perchlorate, iron bromide, iron iodide or iron oxalate, thereby causing adhesion of an iron component to the porous silicon oxide, drying the impregnated porous silicon oxide, and then calcining the dry porous silicon oxide in the air at a temperature in the approximate range of 200–800° C., preferably in the approximate range of 300–700° C.

The catalyst precursor having an iron component contained in porous silicon oxide may otherwise be obtained by forming a silicon/iron mixture by the sol-gel process from a solution obtained by mixing at least one member selected from the group consisting of the water-soluble iron compound mentioned above and organic iron compound with tetraethyl silicate as the raw material for silicon, drying the silicon/iron mixture, and calcining the dry mixture in air at a temperature in the approximate range of 200–800° C., preferably in the approximately range of 300–700° C. Organic iron compounds usable herein include ferrocene, iron naphthenate, carbonyl iron, and iron octylate, for example.

The incorporation of the alkali metal (at least one member selected from among lithium, sodium, potassium, rubidium, and cesium) in the catalyst precursor can be achieved by any of various methods. Generally, the catalyst having silicon oxide-iron ion-alkali metal ion as a catalytically active component thereof can be obtained by immersing the catalyst precursor obtained in a powdery formed by the procedure mentioned above in an aqueous solution of such an alkali metal as alkali carbonate, alkali nitrate, or alkali hydroxide, thereby causing adhesion of the alkali metal component to the catalyst precursor powder, drying the wet catalyst precursor, and calcining the dry catalyst precursor in the air at a temperature in the approximate range of 200–800° C., preferably in the approximate range of 300–700° C.

The iron/silicon (atomic ratio) in the catalyst precursor (and the catalyst) is preferably in the approximate range of 1/100000–3/100, more preferably in the approximate range of 1/100000–5/100, and the alkali metal/silicon (atomic ratio) in the catalyst is preferably in the approximate range of 1/10000–5/100, more preferably in the approximate range of 1/1000–1/100.

When the catalyst obtained by the method described above is analyzed using laboratory instruments, it is found that the silicon is in an oxidized state, the iron is in a divalent and/or trivalent oxidized state, and the alkali metal is in a univalent oxidized state and that the iron component and the alkali metal component are uniformly dispersed on the outer surface of the porous silicon oxide (namely a silicon oxide having a high specific surface area), which is the main component of the catalyst, and on the inner surface of the pores therein. It is, therefore, proper to conclude that the catalyst according to this invention is in a state such that the iron component and the alkali metal component are uniformly dispersed in the silicon oxide.

The catalyst according to this invention is used in an arbitrarily form such as, for example, granule, beads, and honeycombs. A shaped article is produced, for example, by a standard method which comprises preparing a carrier by forming such a material as alumina or clay in the shape of beads or honeycombs, coating the carrier with a slurry containing the catalyst according to this invention such as by the wash coat technique, drying the coated carrier at a temperature in the approximate range of 70–100° C., and calcining the dry carrier at a temperature in the approximate range of 400–600° C. A commercially available carrier suitable for the needs of the invention may be used herein in unmodified form. The deposition of the catalyst on the carrier can be achieved by any of various techniques suitable for coating the carrier with the slurry containing the catalyst and the conditions of the drying and calcining operations.

The method for producing acrolein according to this invention will now be described. Specifically, the acrolein is formed by causing a mixed gas of ethane with oxygen to contact the catalyst of this invention described above under a pressure in the approximate range of normal pressure –3 MPa, preferably in the approximate range of 0.1–2 MPa, at a reaction temperature in the approximate range of 250–600° C., preferably in the approximate range of 300–550° C. The mixing ratio of ethane and oxygen, though not particularly critical, is generally in the approximate range of 1:99–99:1 (molar ratio), preferably in the approximate range of 3:97–97:3 (molar ratio). If necessary, steam can be introduced into the reaction system during the reaction for repressing the degradation of the activity of the catalyst by contamination or a diluting gas such as nitrogen, carbon dioxide, or a rare gas can be introduced into the system for controlling the reaction.

The mechanism of the catalyst according to this invention, though not fully understood yet, is thought to be that acetaldehyde is first formed from ethane and oxygen by the action of the iron component and silica and this acetaldehyde then is converted into acrolein by the action of the alkali metal component.

This invention can produce acrolein from ethane, an inexpensive substance, and oxygen on a commercial scale by use of a uniquely constituted catalyst.

When the catalyst according to this invention is used, the selective production of acrolein is heightened under conditions of high reactivity (high temperature and/or low feed rate of raw materials) and the selective production of aldehyde is heightened under the conditions of low reactivity (low temperature and/or high feed rate of raw materials). By adjusting the reaction conditions, therefore, the two compounds can be selectively produced.

EXAMPLES

The features of this invention will now be further clarified through working examples.

Example 1

A catalyst composed of silicon, cesium (Cs/Si atomic ratio=6/1000), iron (Fe/Si atomic ratio=5/10000), and oxygen was produced by the following method.

First, 10 g of silicon oxide (60–220 pm in particle diameter and 400 $m^2/g$ in specific surface area; silica gel made by Merck & Co., Inc.) was immersed in 18 ml of distilled water and left standing therein for 30 minutes. Meanwhile, 0.034 g of iron nitrate nonahydrate was dissolved in 3 ml of distilled water. The resultant aqueous solution was added to the distilled water containing silicon oxide and the mixture was left standing for one hour to incorporate the iron component into the silicon oxide.

Subsequently, the iron component-containing silicon oxide obtained as described above was placed in a drier at 80° C., dried therein for 12 hours, and calcined in the air at 700° C. to obtain a catalyst precursor which was an oxide of Fe/Si having an atomic ratio=5/10000.

To 2 g of the catalyst precursor, 3.6 ml of distilled water was added. Then, an aqueous solution prepared in advance by dissolving 0.0623 g of cesium carbonate in 3 ml of distilled water was added to the catalyst precursor-containing distilled water to incorporate a cesium component in the catalyst precursor.

The resultant cesium-containing catalyst precursor was placed in a drier at 80° C., dried therein for 12 hours, and then calcined in air at 700° C. for 5 hours to obtain a catalyst 1 formed of a silicon type oxide complex having a Cs/Si atomic ratio of 6/1000 and a Fe/Si atomic ratio of 5/10000.

Example 2

A catalyst 2 formed of silicon, potassium (K/Si atomic ratio of 6/1000), iron (Fe/Si atomic ratio of 5/10000), and oxygen was produced by following the procedure of Example 1, except that 0.0139 g of potassium carbonate was used in place of cesium carbonate.

Example 3

A catalyst 3 formed of silicon, rubidium (Rb/Si atomic ratio of 6/1000), iron (Fe/Si atomic ratio of 5/10000), and oxygen was produced by following the procedure of Example 1, except that 0.0298 g of rubidium carbonate was used in place of cesium carbonate.

The catalysts obtained in Examples 1–3 all had specific surface areas that differed from that of the silica by no more than ±5%. This clearly indicates that the catalysts were thermally stable materials.

Example 4

In a fixed-bed flow type tubular reaction device, the catalyst 1 obtained in Example 1 was introduced (0.3 g) and fixed with quartz wool. The upper and lower spaces opposed to each other across the catalyst bed in the tubular reaction device were filled with quartz sand and the temperature of the reaction line was retained at 90° C.

The reaction conditions were: reaction gas composition= 75 mol % of ethane+25 mol % of oxygen, pressure=0.1 MPA, overall gas flow=30 ml/minute, and (specified) gas flow=6000/hour·ml/g catalyst.

The reaction gas and the product of reaction were assayed by three separate methods, i.e., using a gas chromatograph equipped with a hydrogen flame ionization detector and a thermal conductivity detector, using an infrared gas spectrometer, and using a gas chromatographic mass analyzer. The results obtained by the three methods were substantially identical.

The conversion of ethane (%) and the selectivity (%) of acetaldehyde and acrolein were used as criteria for rating the performance of a given catalyst in this invention in accordance with the following definitions.

Conversion of ethane (%)=(Number of mols of consumed ethane/number of mols of supplied ethane)×100

Selectivity of acetaldehyde (%)=(Number of mols of formed acetaldehyde/number of mols of consumed ethane)×100

Selectivity of acrolein (%)=(Number of mols of formed acrolein/number of mols of consumed ethane)×150

The multiplication by the constant 150 in the computation of the selectivity of acrolein is to correct for the difference between the 2 carbon atoms in ethane and the 3 carbon atoms in acrolein.

Table 1 shows the results of the reaction at a reaction temperature of 475° C. The table shows that acetaldehyde and acrolein were formed at substantially equal conversion rates from ethane and oxygen.

Example 5

A reaction was carried out by following the procedure of Example 2, except that the catalyst 2 obtained in Example 2 was used and the reaction temperature was changed to 500° C. or 450° C. The results of the reactions are shown in Table 1.

The results show that the selectivity of acrolein was high at the reaction temperature of 500° C. and the selectivity of acetaldehyde was high at the reaction temperature of 450° C. This indicates that in the reaction using the catalyst 2, the product could be selected by varying the reaction temperature.

Example 6

A reaction was carried out by following the procedure of Example 5, except that the catalyst 3 obtained in Example 3 was used. The results of the reaction are also shown in Table 1. The results show that acrolein was obtained at a selectivity about three times as high as that of acetaldehyde.

TABLE 1

| Example | Reaction temperature (° C.) | Conversion of ethane (%) | Selectivity of acetaldehyde (%) | Selectivity of acrolein (%) |
|---|---|---|---|---|
| 4 | 475 | 2.2 | 22 | 25 |
| 5 | 500 | 5.3 | 6 | 25 |
|   | 450 | 1.0 | 32 | 16 |
| 6 | 475 | 4.1 | 11 | 31 |

What is claimed is:

1. A catalyst for the production of acrolein from ethane as a raw material comprising silicon, iron, an alkali metal, and oxygen, wherein an iron/silicon atomic ratio is in the range of 1/100000–3/100.

2. A catalyst according to claim 1, further comprising silicon oxide, an iron ion, and an alkali metal ion as active components.

3. A catalyst according to claim 1, wherein said silicon, iron, and alkali metal form an amorphous complex oxide.

4. A catalyst according to claim 1, wherein said alkali metal is at least one member selected from the group consisting of lithium, sodium, potassium, rubidium, cesium and a mixture thereof.

5. A catalyst for the production of acrolein from ethane as a raw material comprising silicon, iron, an alkali metal, and oxygen, wherein an alkali metal/silicon atomic ratio is in the range of 1/10000–5/100.

6. A catalyst according to claim 5, further comprising silicon oxide, an iron ion, and an alkali metal ion as active components.

7. A catalyst according to claim 5, wherein said silicon, iron, and alkali metal form an amorphous complex oxide.

8. A catalyst according to claim 5, wherein said alkali metal is at least one member selected from the group consisting of lithium, sodium, potassium, rubidium, cesium and a mixture thereof.

9. A catalyst for the production of acrolein from ethane as a raw material comprising silicon, iron, an alkali metal, silicon oxide and oxygen; wherein said silicon oxide is porous; and wherein said iron component and alkali metal are uniformly dispersed in said porous silicon oxide.

10. A catalyst according to claim 9, further comprising an iron ion and an alkali metal ion as active components.

11. A catalyst according to claim 9, wherein said silicon, iron, and an alkali metal form an amorphous complex oxide.

12. A catalyst according to claim 9, wherein said alkali metal is at least one member selected from the group consisting of lithium, sodium, potassium, rubidium, cesium and a mixture thereof.

13. A method for the production of a catalyst containing silicon, iron, an alkali metal, and oxygen by the steps of impregnating porous silicon oxide with a mixture of an aqueous water-soluble iron compound solution and an aqueous alkali metal solution or sequentially with said two aqueous solutions, thereby inducing adhesion of iron and an alkali component to said porous silicon oxide, and calcining the resultant porous silicon carbide having iron and alkali metal deposited thereon.

14. A method according to claim 13, wherein said water-soluble iron compound is at least one member selected from the group consisting of iron nitrate, iron sulfate, iron chloride, iron phosphate, iron acetate, iron perchlorate, iron bromide, iron iodide, and iron oxalate.

15. A method according to claim 13, wherein said alkali metal is at least one member selected from the group consisting of lithium, sodium) potassium, rubidium, and cesium.

16. A method for producing a catalyst containing ferrosilicon, alkali metal, and oxygen by forming a mixture of silicon and iron by the sol-gel process from a mixture of at least one member selected from the group consisting of water-soluble iron compound and organic iron compound with tetraethyl silicate, drying the resultant mixture, calcining the dried mixture in the presence of oxygen, then impregnating the product of the calcination with an aqueous alkali metal solution, drying the impregnated product of calcination and calcining the dried product of impregnation in the presence of oxygen.

17. A method according to claim 16, wherein said organic iron compound is at least one member selected from the group consisting of ferrocene, iron naphthenate, carbonyl iron, and iron octylate.

* * * * *